(12) United States Patent
Crouzen

(10) Patent No.: US 6,734,670 B2
(45) Date of Patent: May 11, 2004

(54) DETERMINING A SURFACE PROFILE OF AN OBJECT

(75) Inventor: Paulus Carolus Nicolaas Crouzen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/375,804

(22) Filed: Feb. 26, 2003

(65) Prior Publication Data

US 2003/0169035 A1 Sep. 11, 2003

(30) Foreign Application Priority Data

Feb. 26, 2002 (EP) .............................. 02075765

(51) Int. Cl.⁷ .................... G01N 27/82; G01R 33/12
(52) U.S. Cl. .................. 324/240; 324/230; 324/225; 702/38; 702/104
(58) Field of Search ................... 324/225–243, 324/202; 702/38, 104

(56) References Cited

U.S. PATENT DOCUMENTS

| | | | | |
|---|---|---|---|---|
| 4,843,320 A | * | 6/1989 | Spies | ........................ 324/240 |
| 5,373,235 A | * | 12/1994 | Clark et al. | ............ 324/207.16 |
| 6,037,768 A | * | 3/2000 | Moulder et al. | ............. 324/225 |
| 6,285,183 B1 | * | 9/2001 | Collingwood et al. | ...... 324/202 |
| 6,291,992 B1 | * | 9/2001 | van Andel et al. | .......... 324/240 |
| 6,344,741 B1 | * | 2/2002 | Giguere et al. | ............. 324/240 |

FOREIGN PATENT DOCUMENTS

| | | | | |
|---|---|---|---|---|
| GB | 2112944 A | * | 7/1983 | ............. G01B/7/10 |

* cited by examiner

Primary Examiner—N. Le
Assistant Examiner—Darrell Kinder
(74) Attorney, Agent, or Firm—Charles W. Stewart

(57) ABSTRACT

A method of determining a surface profile of an electrically conductive object, using a probe having a transmitter adapted for inducing transient eddy currents in the object, and a receiver which is adapted for providing a signal indicative of a magnetic field property wherein the surface profile is determined by measuring a characteristic value at selected inspection positions at a selected set of inspection points to obtain a set of inspection values, and correcting for any offsets using a calibration function determined from a set of calibration values taken at a set of calibration positions at a calibration point.

14 Claims, 3 Drawing Sheets

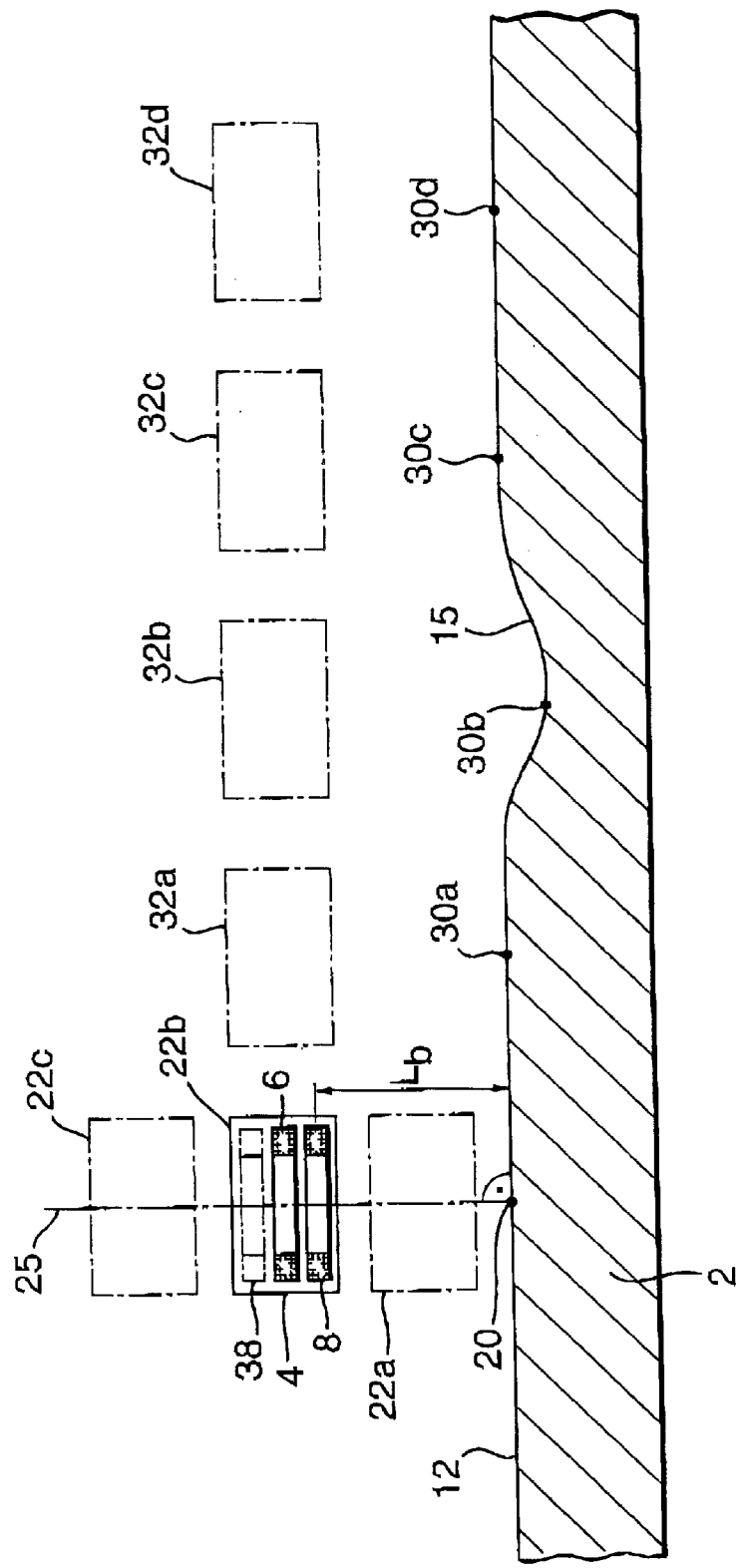

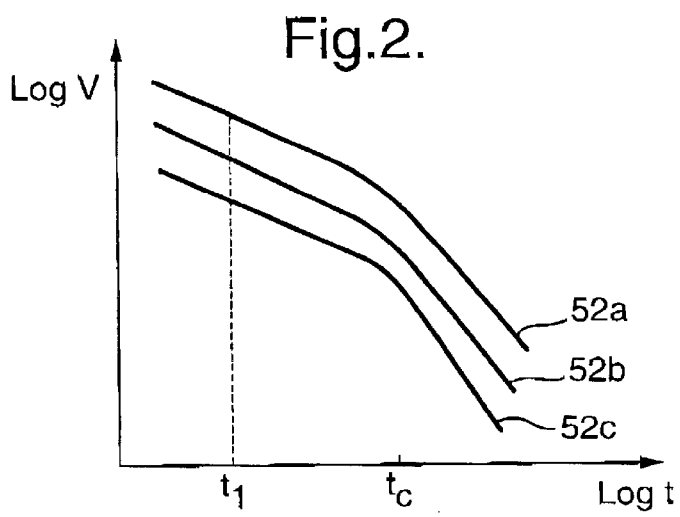
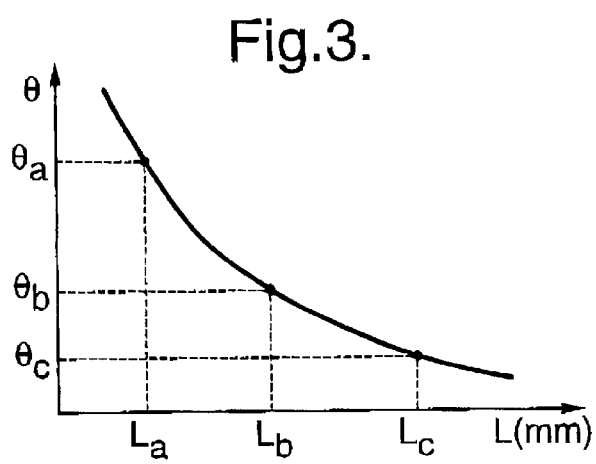
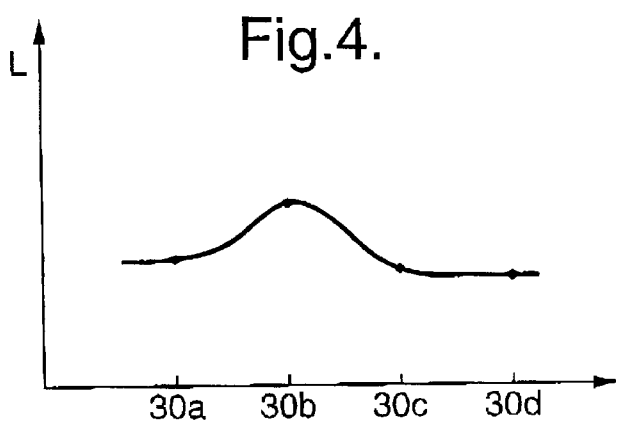

DETERMINING A SURFACE PROFILE OF AN OBJECT

FIELD OF THE INVENTION

The present invention relates to a method of determining a surface profile of an electrically conductive object. In the method a probe is used, which comprises a transmitter/receiver arrangement, wherein the transmitter is adapted to induce transient eddy currents in the object, and wherein the receiver is adapted to provide a signal indicative of the strength of a magnetic field or changes in the strength of a magnetic field. Transient eddy currents are generally induced when the electrically conductive object is subjected to a non-steady changing magnetic filed, such as generated by a coil that is energized by a current pulse. Transient eddy currents change with time after excitation, generally decaying to zero in the absence of further excitation, and so does the signal received in the receiver.

BACKGROUND OF THE INVENTION

Transient eddy-current methods are useful inspection techniques, and examples of objects that can suitably be inspected with the method according to the present invention are metal plates or walls of container means, such as pipes, vessels or containers, having a radius of curvature that is larger than the thickness of the object. The electrically conducting material can be any electrically conducting material, for example carbon steel or stainless steel.

The term surface profile is used in the claims and in the description to refer to a representation of the shortest distance to a surface from known reference points, which are for example arranged along a line or in a plane substantially parallel to the surface to be inspected. A surface profile can reveal surface roughness, and anomalies such as a local decrease of the thickness of the object, which decrease is caused for example by corrosion.

A particularly important parameter which can be derived from a surface profile is the depth of an anomaly. When inspecting for example pipes, the depth of a corrosion spot is a critical parameter for the integrity assessment, since it is related to the remaining wall thickness.

Conventional methods for determining a surface profile are based on ultrasonic measurements at selected inspection points. Ultrasonic measurements cannot differentiate between an electrically conductive object to be investigated, and non-conductive materials covering the object, e.g. thermal insulation, paint, or corrosion products. It is therefore usually required to remove any such non-conductive materials, e.g. by grit blasting. For pipes and vessels operating at high pressures, this usually requires the equipment to be taken out of service, since safety considerations often forbid any in-service surface preparation. It may be particularly hazardous to remove corrosion products, since this may trigger a leakage. There is a need for novel non-invasive inspection methods, which would permit continued operation.

European patent specification No. 321 112 discloses a method of determining the thickness of a container wall means under insulation. In the known method, a probe is used comprising a transmitter coil for inducing eddy currents in the object, and a receiver system for providing a signal indicative of changes in the strength of a magnetic field. The known method comprises inducing transient eddy currents in the object; receiving a signal indicative of the eddy current, and comparing the decay of the received signal over a period of time with a reference decay indicative of a known wall thickness, whereby the thickness of the container means wall portion can be inferred.

When inspecting an object for corrosion, it is often not needed to actually determine the thickness of the object or of its wall. Rather, it will often be sufficient to inspect the surface that is accessible with a measuring instrument for irregularities and anomalies. This is particularly interesting for objects that have a substantially smooth surface profile at the time of installation, as is usually the case with pipelines or container walls. By measuring a surface profile later on, corrosion spots can be detected.

It would be advantageous to provide a new method for determining the surface profile of an electrically conductive object.

SUMMARY OF THE INVENTION

The invention relates to a method of determining a surface profile of an electrically conductive object, using a probe comprising a transmitter which is adapted to induce transient eddy currents in the object, and a receiver which is adapted to provide a signal indicative of the strength of a magnetic field or changes in the strength of a magnetic field, the transmitter and receiver forming a transmitter/receiver arrangement, according to the present invention comprises the steps of:

(a) selecting a calibration point on the surface, and selecting a number of calibration positions of the transmitter/receiver arrangement relative to the calibration point;
(b) determining a set of calibration values by determining, for each of the calibration positions, a characteristic value of the signal generated in the receiver in response to transient eddy currents induced in the object by the transmitter, wherein the characteristic value relates to the amplitude of the signal;
(c) determining a calibration function which relates the calibration values to the relative location of calibration position and calibration point;
(d) selecting a set of inspection points on the surface of the object, and selecting a set of inspection positions of the transmitter/receiver arrangement in correspondence to the set of inspection points;
(e) determining a set of inspection values by determining, for each of the inspection positions, a characteristic value of the signal generated in the receiver in response to transient eddy currents induced in the object by the transmitter; and
(f) determining the surface profile by interpreting the set of inspection values, wherein the calibration function is taken into account, and wherein the relative location of inspection points and corresponding inspection positions is derived.

BRIEF DESCRIPTION OF THE DRAWINGS

FIG. 1 shows schematically a first embodiment of the invention;

FIG. 2 shows schematically signals generated in a receiver for different vertical positions of a transmitter/receiver arrangement above an object;

FIG. 3 shows schematically an example of a calibration curve representing a calibration function;

FIG. 4 shows a surface profile of the object shown in FIG. 1;

DETAILED DESCRIPTION OF THE INVENTION

Figure 5:
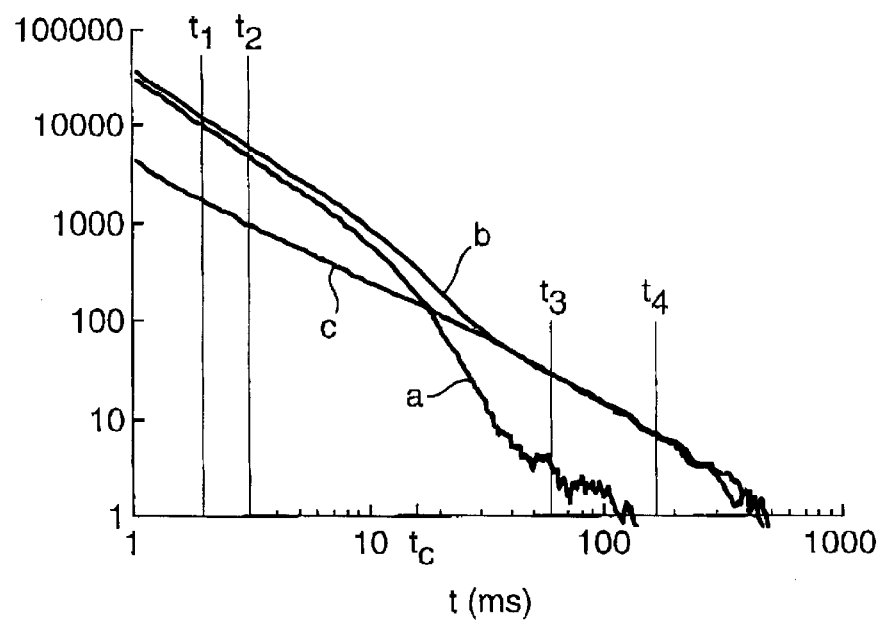
FIG. 5 shows an example of signals registered for a steel pipe (a), a steel pipe with corrosion products (b), and corrosion products alone (c)

The invention is based on the insight gained by Applicant, that the overall amplitude of a signal received by a probe in response to transient eddy currents in an object, can be used to quantify the distance between the probe and the object. By performing measurements systematically at a number of selected inspection positions, a surface profile can thus be obtained.

The transmitter/receiver arrangement can comprise a further (second) receiver, spaced apart from the first receiver, and the calibration values and the inspection values are in this case determined from the signals generated in the first and second receivers at the respective position of the transmitter/receiver arrangement. Such a transmitter/receiver arrangement is particularly useful when it is oriented such that the first and second receivers are spaced substantially along the normal to the surface at the point to be investigated, and when the calibration values and inspection values relate to a ratio of characteristic values of the signals generated in the first and second receivers.

When inspection values are obtained for more than one inspection position of the transmitter/receiver arrangement, or for more than one position of a receiver, corresponding to an inspection point, the inspection values can be interpreted so as to determine a parameter that is a measure of an electromagnetic property of the object at the inspection point.

Suitably, the method of the present invention can be used to determine a correction for conventional wall thickness measurements, wherein a wall thickness has been determined from a characteristic of the signal at any one of the inspection positions corresponding to the inspection point, wherein in the correction the determined parameter that is a measure of an electromagnetic property of the object at the inspection point is taken into account.

In practically very important applications of the present invention, the electrically conductive object is covered with corrosion products at one or more inspection points, and one is interested in the true surface profile of the object underneath the corrosion products. Accordingly, the present invention also provides a method for determining a surface profile underneath corrosion products, wherein the method further comprises obtaining a signal representing the response generated by isolated corrosion products in the receiver to pulsed energizing of the transmitter; and applying a correction to account for the signal contribution from corrosion products to the total signal received at an inspection position corresponding to the corroded inspection point.

The correction suitably comprises comparing the total signal and the signal representing isolated corrosion products at a time or in a time interval where the signal contribution from corrosion products dominates the total signal. A corrected signal pertaining to the corroded inspection point can be obtained, in which corrected signal the contribution of corrosion products has been eliminated, so that the inspection value pertaining to the corroded inspection point can be determined by determining the characteristic value of the corrected signal.

International patent application publication No. WO 02/16921, which was unpublished at the priority date of the present application, discloses a method of inspecting an electrically conductive object so as to detect the presence of an anomaly, wherein pulsed eddy current signals are acquired for a number of inspection points on the object. The method provides a qualitative indication of the presence of an anomaly, if a characteristic value of one of the signals differs significantly from a norm. In an article "Conformable array for mapping corrosion profiles" by A. E. Crouch and P. C. Porter, which article was retrieved from the Internet on 3 Oct. 2002, and which article refers to the 14th Annual Pipeline Pigging, Integrity Assessment & Repair Conference, Houston, 23–24 Jan. 2002, a conformable sensor coil array is described, which can be used for pipeline inspection. The operation of the array is not based on exciting transient eddy currents and following the accompanying signal over time as in the present invention. Rather, the sensor coils are activated by an alternating current of a selected frequency, for an extended period of time, thereby generating steady-state eddy currents in the inspected object. By analysing the complex impedance of the coils, prefabricated defects in a steel test object could be detected. The influence of corrosion products on the measurements is not discussed.

Reference is now made to FIG. 1. The object of electrically conducting material is referred to with reference numeral 2 and the probe is referred to with reference numeral 4. The probe 4 comprises a transmitter/receiver arrangement having a transmitter coil 6 for transmitting an electromagnetic field and a receiver coil 8. The transmitter coil 6 is connected to a device (not shown) for energizing the transmitter coil and the receiver is connected to a device (not shown) for recording the signals from the receiver.

The distance between a selected point in the probe 4 and the surface 12 of the object 2 is denoted by L, and part of the space between the probe 4 and the object 2 is for example filled with paint, or with an insulation layer (not shown) covering the surface 12. The surface 12 is the surface of the object nearest to the probe. The object 2 has an anomaly at the surface 12, which anomaly is being referred to with reference numeral 15.

In order to determine the profile of the surface, first a calibration is performed. To this end a calibration point 20 is selected on the surface 12, suitably in an area of the surface without anomalies. A set of calibration positions of the probe 4 including the transmitter/receiver arrangement are selected relative to the calibration point 20, suitably at different distances L along the normal of the surface. Three calibration positions 22a, 22b, and 22c are indicated in FIG. 1, which are separated along the normal 25 through the surface at the calibration point 20. A suitable way to arrange the probe at the different calibration positions is for example to place plastic spacers or stacks of plastic spacers of known thickness on the surface, and to place the probe on top thereof.

Then, a set of calibration values corresponding to the set of calibration positions is determined. To determine a calibration value, the probe 4 is placed at one of the calibration positions, for example at position 22b, having a distance $L_b$ from the surface 12. Eddy currents are induced in the object by energizing the transmitter coil 6 with a current I during a finite time interval. Suitably, time interval is chosen so long, that eddy currents generated due to the switch-on of the current I have died out. After the current I has been switched off, eddy currents are generated again in the object 2, and cause a changing magnetic field at the location of the receiver coil 8, thereby inducing a voltage V in the receiver coil.

FIG. 2 shows schematically signals 52a, 52b, 52c which can be obtained when the voltage V, measured at the receiver coil 8 is registered as a function of time t after the current I has been switched off, when the probe 4 is in the calibration positions 22*a* (distance $L_a$), 22*b* (distance $L_b$), and 22*c* (distance $L_c$), respectively. FIG. 2 illustrates, in a double logarithmic representation, that the overall amplitude of the signal increases with decreasing distance between the receiver coil 8 in the probe 4 and the surface 12, i.e. that for a selected time the signal is the stronger, the closer the receiver coil is located to the surface. The signals shown in FIG. 2 exhibit a decay rate that is slower in the initial part of the curve, and faster for times greater than a critical time $t_c$. The critical time $t_c$ reflects the time it takes for the eddy currents diffuse from one surface of the wall to the other, and is therefore a measure for the thickness of the object 2.

It is not generally needed to acquire the entire time signal as shown in FIG. 2, in order to determine a characteristic value that relates to the overall magnitude (amplitude) of the signal. The overall magnitude of the signal can already be derived from the initial part of the signal, long before the critical time $t_c$ (which is in the order of some 10 ms for steel objects of several millimeter thickness). So in order to determine a surface profile it is not generally needed for the eddy currents to diffuse through the object. Wall thickness measurements always require measurement times long enough for the eddy currents to diffuse through the object. Therefore, if only the initial part of the signal is used, the method has the additional advantage of shorter measurement times as compared with wall thickness measurements. It was also found, that by analysing the amplitude of the received signal smaller surface anomalies can be analysed than with wall thickness measurements.

The skilled person will understand that there are various ways in which a characteristic value can be determined, which is related to the amplitude of the signal. For example, the voltage $V(t_1)$ at a selected time $t_1$ can be registered, preferably in the initial part of the signal where the signal is strongest.

Then, a suitable characteristic value θ can be defined as:

$$\theta = \frac{V(t_1)}{I}, \quad (1)$$

wherein I is the energizing current of the transmitter coil. Throughout the specification and the claims units for voltages are volts, units for currents are Ampere, and units for times are seconds, units for distances are meters.

It is also possible to register the voltage signal $V(t_i)$ at different times $t_i$ (i=1, . . . , n), and to replace $V(t_1)$ in equation (1) by a summation $$\sum_{i=1}^{n} V(t_i),$$

or by an integration of the voltage over a selected time interval of the signal. In all cases, a characteristic value is obtained that relates to the overall amplitude of the signal.

FIG. 3 shows a plot of the characteristic values $\theta_a$, $\theta_b$, $\theta_c$ determined for the calibration positions 22*a*, 22*b*, 22*c* of FIG. 2, in dependence of the corresponding distances from the surface. It shall be clear that more calibration values at other calibration positions can be obtained. The solid curve shown in FIG. 3 is a representation of the calibration function, which relates the characteristic value to the relative location of calibration point and calibration position.

Returning now to the discussion of FIG. 1, after the calibration values have been determined, a number of inspection positions are selected on the surface 12. For the sake of clarity, FIG. 1 shows only four inspection points 30*a*, 30*b*, 30*c*, and 30*d* in a linear arrangement on the surface 12. It shall be clear, that in practice more points and other arrangements such as matrix arrangement can be selected.

Corresponding to the inspection points, a number of inspection positions of the transmitter/receiver arrangement are selected. In FIG. 1 there are indicated four positions 32*a*, 32*b*, 32*c*, 32*d* of the probe 4 including the transmitter/receiver arrangement, which positions are arranged along a line, the normal projection of which onto the surface 12 substantially coincides with the path connecting the inspection points.

For each of the inspection positions, an inspection value is determined. Suitably, energizing of the transmitter, receiving of the signal and calculation of the inspection value from a characteristic value of the received signal is done in the same way as for determining the calibration values. Like the calibration value, the inspection value also relates to the amplitude of the respective signal.

Using the calibration function previously obtained, as represented by FIG. 3, for each of the inspection positions the distance, calculated from a selected point in the probe, above the respective inspection point can be determined. This can for example be done by linear interpolation. Since the location and orientation of the transmitter/receiver arrangement at the corresponding inspection position in space are known, deriving the distance corresponds to deriving the relative location of inspection point and the corresponding inspection position.

FIG. 4 shows the resulting surface profile, wherein on the abscissa the inspection points are indicated, and on the ordinate the determined distance between corresponding inspection points and inspection positions. In order to derive a quantitative surface profile, the known relative position of the inspection positions with respect to each other is taken into account.

Several modifications and suitable embodiments of the invention outlined above will now be discussed.

The calibration function can suitably be represented by an analytical function, in order to facilitate evaluation with a computer. The analytical function can in particular be determined on the basis of a theoretical approach, this has the advantage that fewer calibration values have to be determined.

A theoretical expression has been derived under the assumption that the object has a plane surface, and that the eddy currents generated in the object circle about the normal to the surface at the calibration point within a radius R, such that the strength of the eddy currents $I_{ec}$, in dependence of the radius r from the normal, is $I_{ec}(r)=I_{ec0}$ for $r \leq R$ and $I_{ec}(r)=0$ for $r>R$, wherein $I_{ec0}$ is a constant eddy current. Then, the characteristic value θ as defined in equation (1) is obeys the following relationship:

$$\theta(z) = \alpha \left[ \log\left( \frac{R + \sqrt{R^2 + z^2}}{|z|} \right) - \frac{R}{\sqrt{R^2 + z^2}} \right], \quad (2)$$

wherein
z is the distance of the probe (receiver) from the calibration point along the normal to the surface, and
α is a dimensionless proportionality constant that accounts for instrumental factors such as size and number of turns of the receiver coil, and gain of electronic amplifiers in the receiver, and that is moreover a measure of electromagnetic properties of the test object, in particular of the product $\sigma.\mu$ of the electric conductivity $\sigma$ (units $Ohm^{-1}.m^{-1}$) and the magnetic permeability $\mu$ (units $V.s.A^{-1}.m^{-1}$) of the material of the object.

It was found, that there is good agreement between calibration values determined according to equation (1) in practical experiments and the theoretical expression (2), if suitable values for R and $\alpha$ are chosen. R and $\alpha$ can for example be determined by a least-squares fitting of equation 2 to a limited number of calibration values, together with the known distances between calibration positions and the calibration point. Equation (2) can be inverted such that the distance z can be determined in dependence of an inspection value measured at an inspection position.

In the examples discussed hereinbefore, the transmitter/receiver arrangement is formed by a single transmitter coil and a single receiver coil, stacked parallel to each other. Different transmitter/receiver arrangements can also be used. The receiver coil can be oriented perpendicular to the transmitter coil, and they can be laterally spaced with respect to the surface of the object to be investigated. It is also possible to use a single coil serving initially as transmitter of a magnetic pulse, and then as a receiver of the magnetic field generated by the eddy currents.

A particularly useful transmitter/receiver arrangement comprises two spaced apart receivers. FIG. 1 indicates at reference numeral 38 a second receiver coil, which is arranged parallel and co-axially to the first receiver coil 8. The total signal generated in the receiver in this case comprises the signal generated in the first receiver coil 8 and the signal generated in the second receiver coil 38. The receiver coils are suitably spaced apart by a distance in the order of the diameter of the receiver coils.

By arranging two spaced apart receivers, it is possible to measure a property of the magnetic field, caused by the eddy currents in the object 2, at different distances from the surface 12. In particular, when two substantially identical receivers are so arranged that they are spaced along the normal to the surface, the gradient of the property of the magnetic field can be determined from the gradient in the signals received in the two receivers. When the receivers are receiver coils, the distance of the receiver coil that is closer to the surface from the surface is selected to be approximately in the order of the diameter of the receiver coils.

Suitably, in this case the ratio of first and second characteristic values $\theta'$ and $\theta''$ of the signals generated in the first and second receiver, respectively, is evaluated. For example, when a characteristic value for each of the signals is determined according to equation (1) using the same time $t_1$, one obtains $$\frac{\theta'}{\theta''} = \frac{V'(t_1)}{V''(t_1)}, \quad (3)$$

wherein $V'(t_1)$ and $V''(t_1)$ are the voltages measured at time $t_1$ at the first and second receiver coils, respectively. It shall be clear that it is also possible to register voltage signals $V'(t_i)$ and $V''(t_i)$ at different times $t_i$ (i=1, ..., n), and to replace $V'(t_1)$ and $V''(t_1)$ in equation (1) by a summation of the registered voltages, or by an integration over a selected time interval.

Such a ratio of characteristic values can be used to determine the calibration values and measurement values in the method of the present invention. Each of the characteristic values relates to the signal amplitude of the signal generated in the first, or second, receivers. The skilled person will understand that it is not required to explicitly determine the first and second characteristic values separately. It is sufficient for the method of the present invention that they are implicitly represented in the calibration values and inspection values that are determined, for example when an electronic circuit is used that performs a division of voltages $V'(t_1)$ and $V''(t_1)$.

The ratio of characteristic values represents a gradient in a property of the magnetic field, e.g. the magnetic field strength or the time—change of the magnetic field strength. It shall be clear that a gradient can also be defined in a different way, e.g. as a difference of signals divided by the distance of the receiver coils.

That such a gradient can be used to determine the distance of the probe to the surface can be explained as follows. Referring again to FIG. 1, when a calibration measurement is performed with the probe above the calibration point 20, the magnetic field due to the eddy currents in the object 2 is strongest near the surface 12, and gradually decreases to zero far away from the object 2. The gradient of the magnetic field is thereby greatest close to the surface, and smaller at larger distances. When the probe is in calibration position 22a, the two receiver coils are close to the object, and the difference in the magnetic field between the two positions of the receiver coils is relatively large. As a result, there will be a large difference between the signals generated in the two receiver coils, and therefore a large ratio of characteristic values $\theta'/\theta''$. When, on the other hand, the probe is placed at position 22c, the gradient of the magnetic field is much smaller, so the two receivers will be exposed to (nearly) the same field strength and therefore receive nearly the same signal. A calibration function can be obtained relating the ratio of characteristic values $\theta'/\theta''$ to the distance from the surface, similar to the calibration function represented by FIG. 3. Using this calibration function, an unknown distance between an inspection position and an inspection point can be derived.

Also in the case of two receivers it is possible to determine an analytical expression for the calibration function, for example for the case described in relation to equation (2) one obtains:

$$\frac{\theta'(z+\Delta)}{\theta''(z)} = \frac{\left[\log\left(\frac{R+\sqrt{R^2+(z+\Delta)^2}}{|z+\Delta|}\right) - \frac{R}{\sqrt{R^2+(z+\Delta)^2}}\right]}{\left[\log\left(\frac{R+\sqrt{R^2+z^2}}{|z|}\right) - \frac{R}{\sqrt{R^2+z^2}}\right]}, \quad (4)$$

wherein $\Delta$ is the distance between the receivers, and wherein the other symbols have the same meaning as defined before.

Equation (4) does not contain the proportionality constant $\alpha$ anymore. This illustrates an important advantage of the measurement using two receiver coils, namely that the measurements are far less dependent on the electromagnetic properties of the test object.

The electromagnetic properties of an object to be tested, in particular the product $\sigma.\mu$ as defined before, may vary between different inspection points and the calibration point. This is a source of error in inspection methods based on transient eddy currents, which generally limits the accuracy of quantitative measurements. The method of the present invention, wherein two spaced apart receivers are used and wherein the gradient of the magnetic field due to eddy currents is evaluated, allows to determine the surface profile with higher accuracy, wherein the influence from changing electromagnetic properties is taken into account.

It is noted that the factor R in equations (2) and (4) may vary somewhat with the electromagnetic properties and the geometry of the test specimen. This effect can further be taken into account when one or more further receiver coils are arranged, spaced apart from the first and second receiver coils. By combining pairs of characteristic values determined by using the individual receiver coils, two or more independent equations analogous to equation (4) can be obtained, from which both R and z can be solved.

The method of the present invention can be used to determine a parameter that relates to an electromagnetic property of the object at the point of the surface that is being inspected. It has been discussed with reference to FIG. 2 how the parameter α can be determined from measurements at different calibration positions of the transmitter/receiver arrangement corresponding to a calibration point. Similarly, on the basis of equation 2 also measurements can be evaluated wherein the transmitter coil is kept stationary, and wherein characteristic values of signals at different distances of a receiver from the point at the surface are obtained.

When the value of the parameter α has been determined for a calibration point at the surface, where $\alpha=\alpha_{cp}$, and for an inspection point, where $\alpha=\alpha_{ip}$, these values can be used to determine a corrected wall thickness at the inspection point. This will be explained hereafter.

When measuring an unknown wall thickness, there are three wall thicknesses, (1) the actual wall thickness or true wall thickness, (2) the measured wall thickness (before correction) and (3) the corrected wall thickness. Correcting the measured wall thickness is done in order to get a wall thickness that is nearer to the actual wall thickness than the measured wall thickness before correction.

It is known in the art how a wall thickness can be determined from a characteristic of the signals generated in any one of the receivers discussed hereinbefore, which signals generally have the shape shown in FIG. 1.

In one known method, the critical time of the signals that was already discussed with reference to FIG. 1, is quantitatively evaluated. Another method includes calculating the integral of the signals in time between two predetermined times and obtaining information on the thickness from the calculated value. A further method is based on determining the time that it takes for the signal to decrease from a first value to a second value and obtaining the thickness from a relation between wall thickness and this time.

All these methods are based on a calibration using measurements on an object with known wall thickness, and as such they provide a measured wall thickness $WT_m$ at the inspection point that is not corrected for the influence of different electromagnetic properties at the calibration point and at the inspection point.

A corrected wall thickness $WT_c$ at the inspection point, wherein the influence of different electromagnetic properties is taken into account can suitably be determined from the relationship $$WT_c = WT_m \frac{\sqrt{\alpha_{ip}}}{\sqrt{\alpha_{cp}}}. \quad (5)$$

According to another aspect of the present invention, the influence from corrosion products can be taken into account. This aspect of the invention is particularly important when it is undesirable to remove the corrosion products, e.g. by grit-blasting. For example, if a corroded steel object is to be inspected which is operated at high internal pressure, mechanical removal of the corrosion products can further weaken the structural integrity before the severity of corrosion has be assessed. In such situations a method is required that can measure the true surface profile of the electrically conductive object underneath the corrosion products. It has been found, that corrosion products of steel, when subjected to a transient eddy current measurement, produce a signal in the receiver although they are non-conductive. Corrosion products are therefore a source of error in eddy current measurements of corroded objects. The signal from the corrosion products contributes to the total signal of the corroded object, whereas one is normally only interested in the signal from the uncorroded part of the object, in order to determine a surface profile, or a wall thickness thereof.

FIG. 5 illustrates the signal contribution from corrosion products. Transient eddy current signals are shown in arbitrary units as a function of time t. Curve a) shows the signal received from a 6.5 mm thick steel sample, wherein the probe was located 22 mm above the nearest surface of the sample. Curve b) shows the total signal that is received when a 12 mm thick layer of corrosion products is deposited on the steel sample, wherein the distance between probe and the surface of the steel sample as well as all other measurement conditions are kept constant with respect to the measurement of curve a). The distance between the probe and the near surface of the corrosion product layer in this experiment was therefore 22 mm−12 mm=10 mm. Curve c) shows the signal that is received from a 12 mm thick layer of corrosion products alone, when the probe is located 10 mm above the near surface of the layer. It is found that the sum of curves a) and c) corresponds well with curve b).

Generally, it was found that the overall shape of the signal received from steel corrosion products is relatively independent of the exact chemical composition, the thickness and the shape of the corrosion products.

FIG. 5 shows, that the corrosion products contribute to the overall amplitude of the signal. The contribution to the total signal in curve b) is relatively smallest in the initial part, and strongest in the late time portions, beyond the critical time. From about 30 ms onwards in FIG. 5, the signal from corrosion products is the dominant contribution to the total signal. The late time portions can therefore be used to adapt the method of the present invention so as to correct the signal for the influence from corrosion products, so that the true underlying profile of the electrically conducting (steel) surface can be obtained. This is suitably done by comparing the total signal of a corroded surface with a signal representing isolated corrosion products at a time or in a time interval where the signal contribution from corrosion products dominates the total signal. In this way the contribution of corrosion products to the total signal can be determined, and a corrected signal can be determined wherein the contribution from corrosion products has been eliminated. Suitably, therefore, when corrosion products are present at one or more of the inspection locations at which a surface profile is to be determined, such a corrected signal determined for each of those inspection locations, and characteristic values of the corrected signals are used to determine the inspection values and thereby the surface profile. The corrected signal can be calculated as a difference between the total signal, and the signal representing the response generated by isolated corrosion products multiplied with a weighing factor. The weighing factor can be determined by comparing of the total signal and the signal representing isolated corrosion products, at a time or in a time interval where the signal contribution from corrosion products dominates the total signal.

A suitable way to do this will now be explained. In this example it is assumed that a transmitter/receiver arrangement with a single receiver coil is used. The total signal of conducting object and corrosion products is measured as voltage $V(t_i)$ at the receiver coil, at various times $t_i$ between times $t_1$ and $t_2$ in the initial part of the signal dominated by the magnetic field of the eddy currents in the conductive object, and between $t_3$ and $t_4$ in the late time portion, where the total signal is dominated by the signal contribution from corrosion products, which late time portion is normally beyond the critical time. An example of the times $t_1$, $t_2$, $t_3$ and $t_4$ is shown in FIG. 5. The characteristic value of the signal is then calculated as $$\theta = \frac{\frac{1}{t_2 - t_1}\sum_{t_1}^{t_2} V(t_i) - \frac{\lambda}{t_4 - t_3}\sum_{t_3}^{t_4} V(t_i)}{I}, \quad (6)$$

wherein $\lambda$ is a dimensionless parameter which will be explained below, and wherein the other symbols have the same meaning as given before.

The parameter $\lambda$ serves to correct for the influence of the corrosion products. The parameter is determined from a signal representing the signal obtained from isolated corrosion products. The signal of voltages $V_c$ (wherein the index c indicates corrosion products) is generally similar to curve c) in FIG. 5. Usually it is possible in practice to remove a small piece of corrosion products from the object for such a reference measurement, which is suitably performed analogous to the measurement of the total signal described hereinbefore. If this is not possible, than in principle a reference measurement obtained on other steel corrosion products can be used. The parameter $\lambda$ is then calculated using the equation $$\lambda = \frac{(t_4 - t_3)\sum_{t_1}^{t_2} V_c(t_i)}{(t_2 - t_1)\sum_{t_3}^{t_4} V_c(t_i)}. \quad (7)$$

Using this $\lambda$, the contribution of corrosion product cancels in the determination of the characteristic value $\theta$ in equation (6).

It shall be clear that the method of correcting the total signal for the contribution due to corrosion products, as described hereinbefore, can in general be applied to transient eddy current signals, independently of the method for determining a surface profile.

EXAMPLE

The surface profile on a naturally corroded defect (anomaly) in a steel pipe was determined. The defect is approximately round and has a diameter at the steel surface of about 35 mm. Initially, corrosion products were removed from the defect. The defect depth was then determined with ultrasonic measurements, and was found to be 7.9 mm.

A probe as shown in FIG. 1 was used, comprising a single receiver coil.

The parameter $\lambda$ was determined from the a measurement on the corrosion products alone, similar to the example shown in FIG. 5, curve c), for the time intervals $[t_1,t_2]=[2\ ms,3\ ms]$ and $[t_3,t_4]=[60\ ms,160\ ms]$. With equation (7), $\lambda$ was determined to be $\lambda=260$.

A calibration point was selected in a non-corroded area of the pipe, and the signal was calibration values were determined for 8 calibration positions, selected between 22 mm and 51 mm above the calibration point. The calibration values were calculated as the characteristic value according to equation (6), wherein $\lambda$ was set to $\lambda=0$ (no corrosion products present on the calibration point), and plotted against the calibration distances so as to obtain a calibration curve as graphical representation of the calibration function.

Then a wooden ruler was put on the outer surface of the pipe, crossing the area of the defect from which corrosion products had been removed. The probe was moved over a plurality of inspection positions on the ruler, where the signal (voltage in the receiver coil) was measured in the time intervals $[t_1,t_2]=[2\ ms,3\ ms]$ and $[t_3,t_4]=[60\ ms,160\ ms]$. A first set of inspection values (set A) was determined according to equation (6), wherein $\lambda$ was set to $\lambda=0$ (no corrosion products present).

Then, the defect was artificially filled with corrosion products, so that a smooth outer surface was created. The probe was moved once again over a plurality of inspection positions on the ruler, where the signal was measured again in the same way and in the same time intervals. From this signal, two further sets of inspection values were determined using equation (6), wherein $\lambda$ was set to $\lambda=0$ for one set (set B, thus no correction for the effect from corrosion products), and to $\lambda=260$ for the other set (set C, with correction for the effect from corrosion products).

Figure 6:
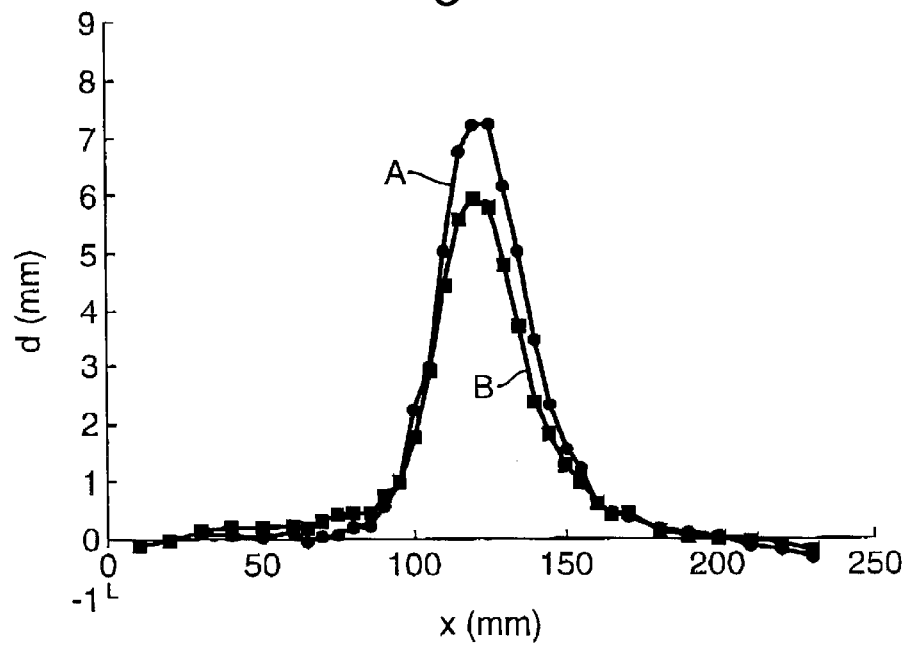
FIG. 6 shows an example of surface profiles determined on a defect in a steel pipe, which was in one case (A) not filled and in the other case (B) filled with corrosion products.

Using each set of inspection values, a surface profile was determined using the calibration curve. The results for the sets A and B are shown in FIG. 6, wherein the coordinate x on the abscissa relates to the position of the probe on the ruler, and wherein the coordinate d on the ordinate relates to the depth from the side of the ruler contacting the surface. The defect depth determined for the case that no corrosion products are present in the defect ('set A') is 7.2 mm, in good agreement with the ultrasonic measurement. When corrosion products are present, but no correction is applied, the defect depth is determined as 5.9 mm. The defect depth is therefore is significantly underestimated in this case. When the surface profile is determined on the basis of set C, a surface profile is obtained that overlays the curve marked A in FIG. 6, and which has consequently not been shown in the figure for the sake of clarity. The effect from corrosion products has thus been corrected for, and a defect depth of 7.4 mm was determined in this case.

It will be understood, that it is also possible to determine a corrected wall thickness, wherein the effect of corrosion products on the signal is taken into account.

It shall be clear that for the method of the present invention a probe can be used, which comprises a plurality of transmitter/receiver arrangements, so that the measurement at various inspection positions (or calibration positions) can be carried out more efficiently than by moving the probe every time.

The receivers for use with the present invention can suitably be coils. In this case the property of the magnetic field that is represented in the signal from the receiver is the change of the strength of the magnetic field with time. Alternatively, the receivers can be Hall effect transducers. When the receivers are Hall effect transducers, or when the signals from the coils are integrated over time, the signals are indicative of the strength of the magnetic field.

What is claimed:

1. A method of determining a surface profile of an electrically conductive object, using a probe comprising a transmitter which is adapted to induce transient eddy currents in the object, and a receiver which is adapted to provide a signal indicative of the strength of a magnetic field or changes in the strength of a magnetic field, the transmitter and receiver forming a transmitter/receiver arrangement, which method comprises the steps of:

(a) selecting a calibration point on the surface, and selecting a number of calibration positions of the transmitter/receiver arrangement relative to the calibration point;

(b) determining a set of calibration values by determining, for each of the calibration positions, a characteristic value of the signal generated in the receiver in response to transient eddy currents induced in the object by the transmitter, wherein the characteristic value relates to the amplitude of the signal;

(c) determining a calibration function which relates the calibration values to the relative location of calibration position and calibration point;

(d) selecting a set of inspection points on the surface of the object, and selecting a set of inspection positions of the transmitter/receiver arrangement in correspondence to the set of inspection points;

(e) determining a set of inspection values by determining, for each of the inspection positions, a characteristic value of the signal generated in the receiver in response to transient eddy currents induced in the object by the transmitter; and (f) determining the surface profile by interpreting the set of inspection values, wherein the calibration function is taken into account, and wherein the relative location of inspection points and corresponding inspection positions is derived.

2. The method of claim 1, in which the receiver forms a first receiver, wherein there is further provided a second receiver spaced apart from the first receiver, the transmitter and the first and second receivers forming the transmitter/receiver arrangement, and wherein the calibration values and the inspection values are determined from the signals generated in the first and second receivers at the respective position of the transmitter/receiver arrangement.

3. The method of claim 2, in which the transmitter/receiver arrangement is oriented such that the first and second receivers are spaced substantially along the normal to the surface at the point to be investigated, and wherein the calibration values and inspection values relate to a gradient in a property of the magnetic field caused by the transient eddy currents.

4. The method of claim 3, in which the gradient is determined as a ratio of the characteristic values of the signals generated in the first and second receivers.

5. The method of claim 1, in which inspection values are obtained for more than one inspection position of the transmitter/receiver arrangement, or for more than one position of a receiver, corresponding to an inspection point, and wherein the inspection values are interpreted so as to determine a parameter that is a measure of an electromagnetic property of the object at the inspection point.

6. The method of claim 5, in which the electromagnetic property is the product of the electrical conductivity and the magnetic permeability.

7. The method of claim 5, further comprising:
determining, for each inspection point, a wall thickness from a characteristic of the signal at any one of the inspection positions corresponding to the inspection point, wherein the determined parameter that is a measure of an electromagnetic property of the object at the inspection point is taken into account.

8. The method of claim 1, in which the surface of the electrically conductive object to be inspected is covered with corrosion products at a corroded inspection point, and wherein the method further comprises:

obtaining a signal representing the response generated by isolated corrosion products in the receiver to pulsed energizing of the transmitter; and applying a correction to account for the signal contribution from corrosion products to the total signal received at an inspection position corresponding to the corroded inspection point.

9. The method of claim 8, in which a corrected signal pertaining to the corroded inspection point is obtained, in which corrected signal the contribution of corrosion products has been eliminated, and wherein the inspection value pertaining to the corroded inspection point is determined by determining the characteristic value of the corrected signal.

10. The method of claim 8, wherein a characteristic value $\theta$ of the total signal is calculated as $$\theta = \frac{\frac{1}{t_2 - t_1}\sum_{t_1}^{t_2} V(t_i) - \frac{\lambda}{t_4 - t_3}\sum_{t_3}^{t_4} V(t_i)}{I},$$

wherein
$t_k (k=1, \ldots, 4)$ are times after the transmitter has been switched off, wherein $t_1 < t_2$ are in the initial part of the signal, and $t_3 < t_4$ are in the late time portion of the signal;

$V(t_i)$ are voltages representing the total signal at the receiver at various moments in time during the time intervals $[t_1, t_2]$ and $[t_3, t_4]$;

I is the current by which the transmitter is energized;

$$\lambda = \frac{(t_4 - t_3)\sum_{t_1}^{t_2} V_c(t_i)}{(t_2 - t_1)\sum_{t_3}^{t_4} V_c(t_i)}; \text{ and}$$

$V_c(t_i)$ are voltages representing the signal at the receiver due to isolated corrosion products, at various moments in time during the time intervals $[t_1, t_2]$ and $[t_3, t_4]$.

11. The method of claim 8, in which the correction comprises comparing the total signal and the signal representing isolated corrosion products at a time or in a time interval where the signal contribution from corrosion products dominates the total signal.

12. The method of claim 11, in which the corrected signal is calculated as a difference between the total signal, and the signal representing the response generated by isolated corrosion products multiplied with a weighing factor, wherein the weighing factor is determined from the comparison of the total signal and the signal representing isolated corrosion products.

13. The method of claim 11, in which the time or the time interval is in the late time portion of the signals.

14. The method of claim 1, in which the time or the time interval is later than about 20 ms after the transmitter has been switched off.

* * * * *